United States Patent [19]

Lynch et al.

[11] Patent Number: 4,923,982
[45] Date of Patent: May 8, 1990

[54] OXIDATION AND REDUCTION METHOD TO PRODUCE 4-ACYLOXYAZETIDIN-2-ONE

[75] Inventors: Joseph E. Lynch, Plainfield, N.J.; William L. Laswell, Perkasie, Pa.; Ralph P. Volante, East Windsor; Ichiro Shinkai, Westfield, both of N.J.

[73] Assignee: Merck & Co., Inc., Rahway, N.J.

[21] Appl. No.: 369,396

[22] Filed: Jun. 21, 1989

[51] Int. Cl.$^5$ .................. C07D 285/10; C07D 501/34; C07D 307/56

[52] U.S. Cl. .................................... 540/200; 540/480; 549/313

[58] Field of Search ................ 540/480, 200; 562/537; 549/313

[56] References Cited

U.S. PATENT DOCUMENTS 3,953,499  4/1976  Pike et al. .......................... 560/121
4,260,618  4/1981  Christensen ........................ 540/200
4,791,207  12/1988  Salzmann et al. ................... 540/200

FOREIGN PATENT DOCUMENTS 0167155  8/1986  European Pat. Off. .

OTHER PUBLICATIONS

Stuart L. Schreiber et al., Tetrahedron Ltrs., vol. 24, No. 23, pp. 2363–2366, 1983.
Bruce H. Lipshutz, Chem. Rev. 1986, 86, 795–819.
Maria Altamura, et al., Syn. Comm., 18(16&17), 2129–2133 (1988).
Klaus Gollnick, et al. Tetrahedron vol. 41, No. 11, pp. 2057 to 2068, 1985.
Masao Shiozaki, et al., Tetrahedron vol. 40, No. 10, pp. 1795 to 1802, 1984.
Paul J. Reider, et al., Tetrahedron Lts., vol. 23, No. 22, pp. 2293–2296, 1982.
Chemical Abstract J6 1243—079—A, dated Jan. 4, 1985, Japan.
Curt Wentrup et al., J. Am. Chem. Soc. 1980, 102, 6161–6163.
Gunda I. Georg, et al., Tetrahedron Ltrs., vol. 26, No. 33, pp. 3903–3906, 1985.
Gunda I.l Georg, et al., J. Am. Chem. Soc. 1987, 109, 1129–1136.
Morrison and Boyd, Organic Chemistry 3rd Ed., Anyn and Bacon, Boston, 1979, pp. 676, 680-1.
Bird et al., Ed. Comprehensive Heterocyclic Chemistry, vol. 4 (Pergamon Press, New York, 1984) pp. 609–611.

Primary Examiner—Mukund J. Shah
Assistant Examiner—E. C. Ward
Attorney, Agent, or Firm—John W. Harbour; Charles M. Caruso

[57] ABSTRACT

The 4-acyloxyazetidin-2-ones, which are intermediates in the production of carbapenems and penems, are produced from 4-furanylazetidin-2-ones by a sequential oxidation-reduction-oxidation reaction scheme.

12 Claims, No Drawings

OXIDATION AND REDUCTION METHOD TO PRODUCE 4-ACYLOXYAZETIDIN-2-ONE

The present invention relates to the preparation of 4-acyloxyazetidin-2-ones. More particularly, the present invention relates to the preparation of the above compounds through a 4-furan-2-ylazetidin-2-one intermediate.

BACKGROUND OF THE INVENTION

Carbapenems and penems are well known antibiotics for treating a broad range of gram-negative and gram-positive bacterial infections.

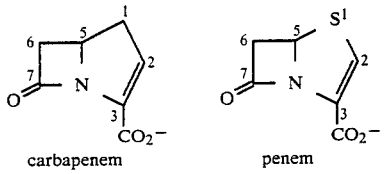

Methods and intermediates for the manufacture of carbapenems and penems are thus matters of scientific and commercial importance.

One method for the production of carbapenems is described in GB No. 2,162,840, Cainelli, et al. As described therein, certain carbapenems are produced from 4-acetoxyazetidin-2-one intermediates.

These intermediates are in turn produced in a multistep synthesis from 4-alkenylazetidin-2-one intermediates of the formula:

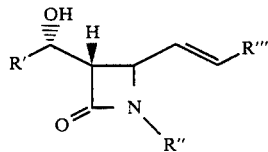

The starting materials to produce the 4-alkenylazetidin-2-one intermediates are:

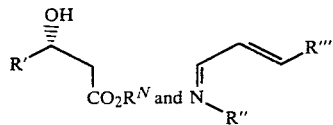

Thus, carbapenems may be produced through two principal intermediates from readily made or available starting materials. However, methods having fewer reaction steps to obtain the intermediates and improved yields are desirable.

Another method for the production of carbapenems is described in EPO No. 0167155, Kan, et al. Again, certain carbapenems are produced from 4-acetoxyazetidin-2-one intermediates. In this case however, these intermediates are in turn produced from 4-triorganosiloxyazetidin-2-one intermediates of the formula:

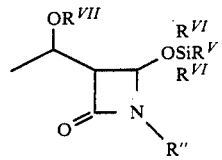

The starting materials to produce the 4-triorganosiloxyazetidin-2-one intermediates are:

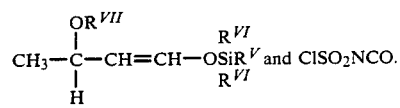

Thus, again, carbapenem may be produced through two principle intermediates from readily made or available starting materials. However, methods having fewer reaction steps to obtain the intermediates as well as methods using less hazardous starting materials than $ClSO_2NCO$ are desired.

A method for the production of penems is disclosed in Christensen, et al., U.S. Pat. No. 4,260,618 from 4-acetoxyazetidin-2-one intermediates. Herein, it is recommended that these intermediates be produced by cleaving penicillin which is produced by fermentation.

It is an object of the present invention to produce 4-acyloxyazetidin-2-one intermediates useful in the production of carbapenems.

It is a further object of the present invention to produce 4-acyloxyazetidin-2-one intermediates from starting materials which are easily handled on account of their low levels of toxicity.

It is yet another object of the present invention to simplify the reactions required and improve the reaction yields in the production of 4-acyloxyazetidin-2-one intermediates.

It is still another object of the present invention to develop a method for the production of 4-acyloxyazetidin-2-one intermediates where an organic group is employed to protect the carbon in the 4-position of the azetidin-2-one and which subsequently may be converted to the 4-acyloxy substitution without replacement.

BRIEF DESCRIPTION OF THE INVENTION

Briefly, there is provided by the present invention a method for the production of 4-acyloxyazetidin-2-ones comprising the steps of:

(a) contacting, at temperatures from about 0°–20° C., an oxidizing combination comprising bromine and sufficient sodium chlorite to produce 4-hydroxylactone azetidin-2-one with 4-furanyl compound of the formula (I):

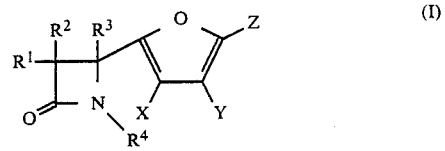

wherein $R^1$ and $R^2$ are independently selected from the group consisting of hydrogen, $C_{1-10}$ alkyl, $C_{1-10}$ fluoroalkyl, alpha-carbon substituted $C_{1-10}$ alkyl, alpha-carbon substituted $C_{1-10}$ fluoroalkyl, where the alpha-carbon substituent is selected from the group consisting of hydroxyl and protected hydroxyl; $R^3$ is selected from the group consisting of hydrogen and $C_{1-10}$ alkyl; $R^4$ is selected from the group consisting of hydrogen and a protecting group for nitrogen; and X, Y and Z are independently selected from the group consisting of hydrogen, halogen, $C_{1-10}$ alkyl, $C_6$ or $C_{10}$ aryl, substituted $C_6$ or $C_{10}$ aryl, $C_{1-10}$ alkoxy, and $C_6$ or $C_{10}$ aryloxy;

(b) hydrogenating the, reaction product of step (a); and (c) contacting the reaction product of step (b) with a peracid to react to acyloxyazetidin-2-one.

DETAILED DESCRIPTION OF THE INVENTION

Herein, $R^1$ and $R^2$ represent those hydrogen, alkyl, and substituted alkyl substituents useful as 6-position substitution on carbapenems. $R^1$ and $R^2$ include, for example, hydrogen, methyl, ethyl, propyl, isopropyl, butyl, isobutyl, $HO-CH_2-$, $CH_3CH(OH)-$, $(CH_3)_2C(OH)-$, $(CH_2)_2C(OH)-$, $CH_3CH_2CH(OH)-$, $CH_3CH_2CH_2CH(OH)-$, $CH_3CH_2CH(CH_3)(OH)-$, $CH_3CH(CH_3)CH(OH)-$, $CF_3CH(OH)-$, $CHF_2CH(OH)-$, $FCH_2CH(OH)-$, $CH_3CHF-$, $F_2CH-$, $F_3C-$, $CH_3CF_2-$, etc.

In preferred embodiments, either $R^1$ or $R^2$ is hydrogen and, in a more preferred embodiment, $R^2$ is beta-hydrogen and $R^1$ is any of the above, excepting hydrogen, in a an alpha orientation. Most preferably, $R^1$ is an alpha oriented 1-hydroxyethyl and $R^2$ is a beta oriented hydrogen.

The protected hydroxy is known in the antibiotic art and refers to a hydroxyl group protected by a suitable protecting radical rendering it inactive during chemical reaction. Of course the identity of this protecting radical will depend on the particular chemical reaction from which the hydroxyl group is being protected. A preferred protecting radical useful herein in the production of the desired 4-acyloxy-azetidin-2-one is dimethyl-t-butylsilyl (TBDMS). This protecting radical may suitable for subsequent reactions of the desired compound or may require replacement depending on the scheme selected to produce penems or carbapenem. Further protecting groups which might be employed include trimethylsilyl, benzyl, p-nitrobenzyl, p-nitrobenzyloxycarbonyl, diphenyl-t-butylsilyl, isopropyldimethylsilyl, phenyl, methyl, etc. Other protecting radicals for hydroxyl groups are known in the art (See T. W. Greene, *Protective Groups in Organic Synthesis*, John Wiley & Sons, Inc., 1981).

$R^3$ may be selected from hydrogen, methyl, ethyl, propyl, etc. Preferably, $R^3$ is hydrogen and has a beta orientation.

As stated above, $R^4$ may be hydrogen or a protecting radical for nitrogen. Suitable protecting radicals for nitrogen include dimethyl-t-butylsilyl, trimethylsilyl, diphenyl-t-butylsilyl, triphenylsilyl, p-nitrobenzyloxycarbonyl, benzyl, f-methoxy phenyl, substituted benzyl etc. As above with the protecting radical for the hydroxyl group, the identity of any protecting radical and whether a protecting radical is at all necessary will depend on the chemical reactions from which the nitrogen group is being protected. For example, herein, the 4-furanylazetidin-2-one is produced by a suggested reaction between a furanyl substituted imine and the derivative of a carboxy compound. In such reaction, the nitrogen of the imine requires a protecting radical such as benzyl. The benzyl may be added to the nitrogen by well known reactions and subsequently replaced with another protecting group or with hydrogen as desired. It is a unique advantage of the process herein to produce 4-acyloxyazetidin-2-one taught herein from 4-furanylazetidin-2-one that no protecting radical is necessary for the nitrogen. Thus, it is preferred in the 4-furanyl azetidin-2-one of formula (1) that $R^4$ is hydrogen. Protecting radicals for nitrogen groups are well known in the art (See also, T. W. Greene, *Protective Groups In Organic Synthesis*, John Wiley & Sons, Inc., 1981).

Suitable X, Y and Z are independently selected from any of hydrogen, methyl, ethyl, propyl, t-butyl, n-butyl, phenyl, p-chlorophenyl, hydroxy, methoxy, ethoxy, phenoxy, etc. Preferably, at least Z is hydrogen. More preferably, X, Y and Z are hydrogen. The principle consideration of selecting X, Y and Z is that they not interfere with the processes taught herein.

Flow sheets A and B depict a suggested synthesis for the starting material described in formula (I). Flow Sheet A depicts the manufacture of an imine. This imine of Flow Sheet A is reacted with a carboxyl derivative in Flow Sheet B to produce the 4-furan-2-yl-azetidin-2-one starting material.

Referring to Flow Sheet A, an available or readily produced furfural 1 is condensed with an amine compound 2. In the case of such condensation, $R^4$ of compound 2 is not hydrogen. Preferably, of course, $R^4$ is a protecting radical for nitrogen and more preferably an organic aromatic protecting radical. Suitable as Compound 2 is benzylamine.

Referring to Flow Sheet B, compound 4 is a readily available or easily produced ester starting material having $R^1$ and $R^2$ substitution or precursors thereof. Suitable ester starting materials as compound 4 include methyl 3-hydroxypropanoate, methyl 3-hydroxypentanoate, methyl 3-hydroxy-4,4,4-trifluorobutanoate, methyl 3-fluorobutanoate, methyl 2-methyl-3-hydroxybutanoate, etc. Preferred is methyl 3-hydroxybutanoate. The nature of the ester group described as methyl is not critical and could be ethyl, propyl, etc.

As the first reaction step of Flow Sheet B, compound 4 is enolized by reaction with a base that generated from n-butyllithium and diisopropylamine in tetrahydrofuran at about $-71°$ C. Subsequently and without isolation of the reaction product, the enolate is quenched by the addition of trimethylchlorosilane (TMSCl), again in tetrahydrofuran at about $-78°$ C., to produce a ketenesilylacetal, compound 5. In this reaction to produce compound 5, any unprotected hydroxy group on either $R^1$ or $R^2$ will be substituted with trimethylsilyl. This is a desirable result as a protecting group will later be necessary on any unprotected hydroxy of $R^1$ or $R^2$. If another type protecting group is desired, it should be added to the hydroxy of compound 4 prior to enolization. If another silyl protecting group is desired, then appropriate replacement should be made for trimethylchlorosilane in the reaction of quenching the enolate.

As the second reaction step of Flow Sheet B, the imine, compound 3, is added to the ketenesilylacetal, compound 5 in dichloromethane at about $-20°$ C. in the presence of trimethylsilyltrifluoromethanesulfonate (TMSOTf). The resultant compound 6 contains $R^1$ through $R^3$ functionality, $R^4$ functionality restricted to protecting radical for nitrogen and the necessary functionality to close the azetidin-2-one ring. At this point or later in Flow Sheet B, the protecting radical for nitrogen, $R^4$, may be converted to hydrogen or some other protecting radical to provide the full spectrum of $R^4$ substitution. For example, a benzyl protecting radical for nitrogen may be substituted with hydrogen through a hydrochloride by hydrogenation ($H_2$/Pd/C) in the presence of HCl and subsequent reaction with sodium hydroxide. Replacement of benzyl with other protecting radicals may be achieved by various methods known to persons skilled in the art.

As the third reaction of Flow Sheet B, compound 6 where $R^4$ is either hydrogen or protecting group for nitrogen according to the above, is saponified to remove the methyl ester and produced compound 7. The saponification is carried out in water, raising the pH to high levels with sodium hydroxide.

Finally, starting material 8 is produced by dehydrating compound 7 to close the azetidin-2-one ring. The dehydration is carried out in 2-propanol with $NaHCO_3$ and methane sulfonylchloride Mes-Cl. A preferred starting material 8 contains an $R^1$ with hydroxy substitution. This hydroxy substitution should be protected as appropriate from reaction conditions in which the starting material 8 is to be employed. The most preferred starting material 8 is shown in Example 6 as compound E9.

Flow Sheet C depicts the process of the invention herein for producing 4-acyloxyaetidin-2-one from starting material 8. In a first and critical reaction, starting material 8 is oxidized to 4-hydroxylactone azetidin-2-one, compound 16. Herein this oxidation is conveniently carried out in a two phase reaction medium having a buffered aqueous phase emulsified by agitation with an organic phase. The organic phase may be chosen from tetrahydrofuran or acetone, but is preferably acetonitrile. To the aqueous phase is added a buffer such as $KH_2PO_4$. In the organic phase is starting material 8. With agitation and cooling, the oxidizing agents bromine and sodium chlorite are added in amounts appropriate to produce 4-hydroxylactone azetidin-2-one. In the case of bromine, this amount is from about 2-150 mole % based on starting material 8 and preferably, 5-15 mole %. In the case of sodium chlorite, this amount is from about 100-200 mole % based on starting material 8. The presence of the sodium chlorite in combination with bromine is critical as too little sodium chlorite will result in an oxidation producing incomplete oxidation products and too much sodium chlorite will produce a 4-carboxy azetidin-2-one. A preferred temperature for the first oxidation ranges from about 0° C. to about 20° C. for a time of from ½ to 2 hours.

The 4-hydroxylactone azetidin-2-one 16 is hydrogenated to 4-acylazetidin-2-one 17 by exposure to pressurized hydrogen gas over an appropriate metal catalyst. The hydrogenation should be performed at about room temperature to prevent thermal degradation of the reactant and product. The resultant 4-acylazetidin-2-one 17 may subsequently be oxidized to a desired 4-acyloxyazetidin-2-one 18 by a Baeyer-Villiger Rearrangement. This type of oxidation is carried out employing a peracid, such as, peracetic acid, perbenzoic acid, permaleic acid, and the like, in an organic solvent, or aromatic hydrocarbons at temperatures of from about 0°-100° C. The 4-acyloxyazetidin-2-one 18 may be converted to other desired 4-acyloxy compounds or to the preferred 4-acetoxy compound 19 employing an excess of the appropriate alkali metal salt of a $C_{1-8}$ organic acid in water. For example potassium acetate may be employed to produce 4-acetoxy compound 19 and sodium benzoate may be used to produce a similar 4-benzoyloxy azetidin-2-one.

Flow Sheet A

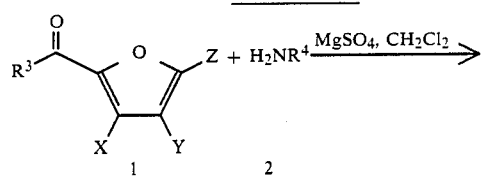

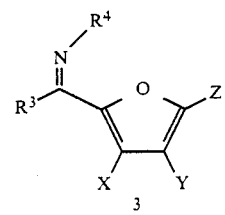

Flow Sheet B

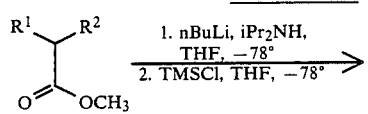

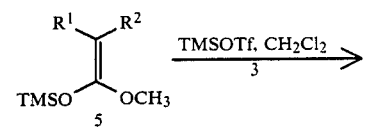

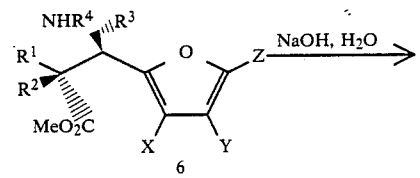

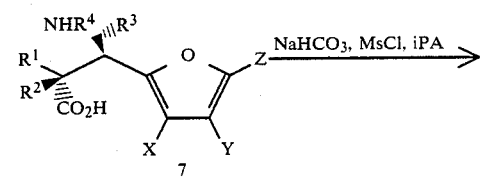

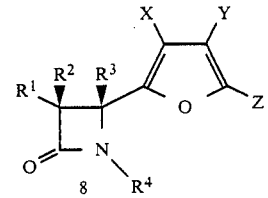

Flow Sheet C

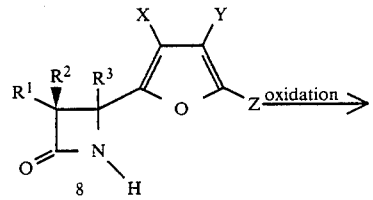

-continued
Flow Sheet C

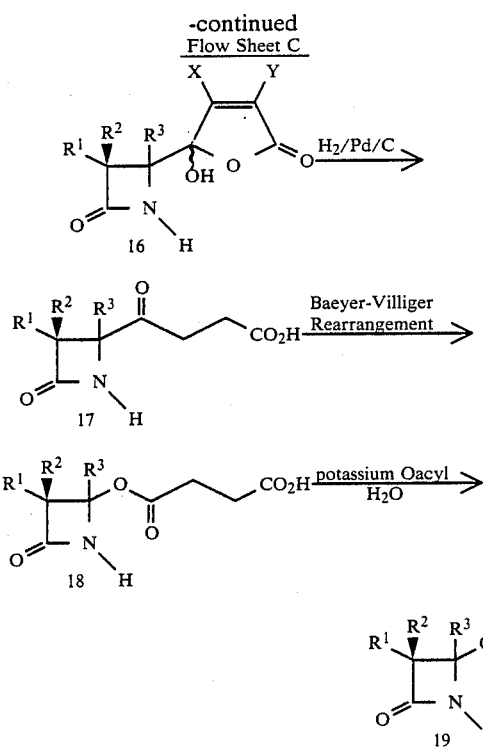

Either of compounds 18 or 19 may be employed to make carbapenems or penems by well known methods. For example, 6-(1'-hydroxyethyl)-2-substituted-pen-2-em-3-carboxylic acid may be made from the above compounds as described in U.S. Pat. No. 4,260,618 hereby incorporated by reference. Therein, a 4-acyloxyazetidin-2-one is reacted with a substituted 1-thienoacetate derivative to provide a seco-lactam. Halogenation of the seco-lactam produces a compound which can be cyclized by treatment with a strong base to the penem. Further use of compounds 18 and 19 to produce carbapenems are taught in Salzman, T. N., et al., J. Am. Chem. Soc., 1980, 102, 6161 and Reider, P. J., et al., Tetrahedron Lett., 1982, 23, 379.

The following examples are illustrative of the best mode of carrying out the instant invention as contemplated by us and should not be construed to be limitations on the spirit or scope of the instant invention.

EXAMPLE 1

(3R)-Z-1-Methoxy-1,3-bis-trimethylsilyloxy-1-butene

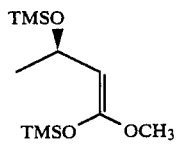

1.54M nBuLi (237 mL, 0.365 mol) was added to diisopropylamine (41.15 g, 0.407 mol) in dry THF (740 ml) at −78° C. under $N_2$. (R) Methyl 3-hydroxybutanoate, E1, (20.00 g, 0.169 mol) in THF (340 mL) was added dropwise such that the temperature did not rise above −71° C. After a 30 minute age chlorotrimethylsilane (40.5 g, 0.373 mol) in THF (100 mL) was added so as to maintain the temperature below −71° C. The solution was stirred at −78° C. for 2 hours warmed to 0° C. and concentrated in vacuo. Hexane (500 mL) was added and the mixture concentrated again. A second portion of hexane (500 mL) was added and the mixture was filtered and concentrated to a pale yellow oil (40.76 g). Distillation gave silyl ketene, E2, as a clear colorless oil b.p. 75°–80° C./0.25 mm (30.32 g, 79%).

EXAMPLE 2

(2S,3R,1"R)-Methyl-2-(1'-N-benzylamino-1'-(furan-2"-yl))-3-hydroxybutyrate

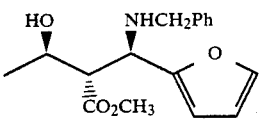

Furfural E3 (4.98 g, 51.8 mmol) was added to benzylamine E4 (5.55 g, 51.8 mmol) in $CH_2Cl_2$ (25 mL). $MgSO_4$ (5 g) was added and the mixture was stirred for 2 hours, filtered and concentrated. The crude oil was redissolved in dry $CH_2Cl_2$ (60 mL) and concentrated repeatedly (2×) until the solution was dry (<10 mg $H_2O/L$). Trimethylsilyl trifluoromethanesulfonate (1.15 g, 5.18 mmol) was added to the imine above in $CH_2Cl_2$ (60 mL) at −20° C., after 5 minutes ketenesilylacetal, E2, (13.6 g, 51.8 mmol) was added and the solution aged for 18 hours. A second portion of ketenesilylacetal, E2, (3.6 g, 13.7 mmol) was added and the solution aged 16 hours. After warming to room temperature the solution was concentrated and redissolved in ethyl acetate (100 mL). The ethyl acetate solution was extracted with 2N HCl (50 mL); the aqueous solution was then treated with 5N $NH_4OH$ to give a pH>9 and was extracted with $CH_2Cl_2$ (50 mL). The $CH_2Cl_2$ solution was dried ($MgSO_4$) and concentrated to give amino ester, E5, as a yellow oil 13.78 g, 87.7%.

EXAMPLE 3

(2S,3R,1"R)-Methyl-2-(1'-amino-1'-(furan-2"-yl))-3-hydroxybutyrate Hydrochloride

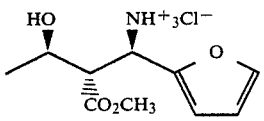

12N HCl (0.48 mL, 5.76 mmol) and 10% Pd/C (170 mg) were added to the amino ester, E5, (1.75 g, 5.76 mmol) in methanol (17 mL). The mixture was hydrogenated at 1 psig $H_2$ at 25° C. until 98% of the starting material had been consumed (HPLC 1:1 $CH_3CN:H_2O$ (0.1% $H_3PO_4$), C8 column, 3 mL/min). The solution was filtered and concentrated to a white solid which was dissolved in 2-propanol (7 mL). Ethylether (30 mL) was then added dropwise with stirring to give hydrochloride, E6, as white needles which were collected on a filter, washed with 4:1 ether:2-propanol (2×5 mL) and dried in vacuo (1.21 g, 79.5%).

EXAMPLE 4

(2S,3R,1"R)-2-(1'-Amino-1'-(furan-2"-yl))-3-hydroxybutyric acid

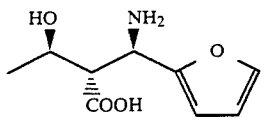

E7

The amino ester hydrochloride, E6, (55.69 g, 0.223 mol) was dissolved in H₂O (225 mL). 5N NaOH was added to pH=12.5; the pH was maintained at pH 12.5 with a pH controller for 18 hours. The solution was then acidified to pH 2 and loaded onto a column of Dowex 50W X 2 resin (700 mL). The column was washed with H₂O (1400 mL) then eluted with 1.5N NH₄OH. The fractions containing the amino acid were concentrated in vacuo to a white solid. 2-Propanol (400 mL) was added and the mixture was concentrated to dryness. The resulting solid was stirred in 2-propanol (400 mL) for 16 hours, collected on a filter, and then dried in vacuo to give amino acid, E7, as an off-white solid (40.99 g, 92.2%).

EXAMPLE 5

(1"R,3S,4R)-3-(1"-Hydroxyethyl)-4-(furan-2'-yl)-azetidin-2-one

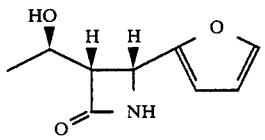

E8

NaHCO₃ (207.7 g, 2.47 mol) and then methanesulfonyl chloride (59.05 g, 0.51 mol) were added to dry 2-propanol (10.3 L). The amino acid E7 (40.99 g, 0.206 mol) was added and the mixture was stirred at 25° C. under N₂ for 39 hours. The mixture was concentrated, and the resulting solid triturated in ethyl acetate (2.5 L). The mixture was filtered and concentrated to a yellow oil (60 g). The oil was dissolved in ethyl acetate (100 mL), stirred with charcoal (3.5 g), filtered and concentrated to 120 ml. Hexane was added to the cloud point and the solution was seeded, hexane (total of 45 mL) was added dropwise. The mixture was stirred at ambient temperature for 1 hour., filtered and the solid was washed with 1:1 hexane:ethyl acetate (2×15 mL) and dried (13.17 g, 35%). The mother liquor was filtered through a short column of silica gel eluting first with 1:1 hexane:ethyl acetate (500 mL) then 1:2 hexane:ethyl acetate (500 mL); the fractions containing the azetidinone were concentrated to an oil that solidified on standing. The solid was broken-up and slurried in 1:1 hexane:ethyl acetate (30 mL), filtered, washed with the same solvent, (10 mL) and dried to give the desired azetidinone, E8, (11.31 g, 31%), total yield 66%.

EXAMPLE 6

(1"R,3S,4R)-2-S(1"-t-Butyldimethylsilyloxyethyl)-4-(furan-2'-yl-azetidin-2-one

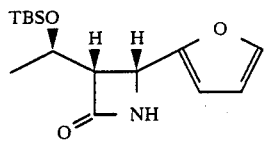

E9

Imidazole (5.63 g, 82.7 mmol) was added to 4-(furan-2-yl)-3-(1-hydroxyethyl)azetidin-2-one, E8, (10.00 g, 55.16 mmol) in dry DMF (25 mL). After cooling to 0° C., t-butyldimethylsilyl chloride (9.14 g, 60.67 mmol) was added, the cooling bath was removed and the solution was stirred at ambient temperature for 18 hours. Hexane:ethylacetate (1:1 75 mL) and water (50 mL) were added; the organic layer was washed with water (2×50 mL), dried (Mg SO₄), and concentrated to give the silyloxy azetidinone, E9, as a yellow oil (16.08 g, 98.6%).

EXAMPLE 7

(1"R,3R,4R)-3-(1"-t-Butyldimethylsilyoxy)-4-(3'-formyl-prop-2'-ene-1'-yl)-azetidin-2-one

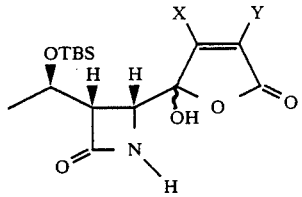

E10

Phosphate buffer was prepared from KH₂PO₄ (54.4 g), H₃PO₄ (1 mL), and H₂O (500 mL). NaClO₂ (80%, 169 mg, 1.5 mmol) was added to the furanylazetidinone E9 (295.6 mg, 1.00 mmol) in CH₃CN (5 mL) and phosphate buffer (5 mL). The mixture was cooled to 0° C. and Br₂ (0.069 mL of 1.45M in CH₃CN, 0.1 mmol) was added. The solution was stirred at 0° C. for 1 hour then acidified with 2N HCl to pH=2. Ethyl acetate (10 ml) was added and the layers were separated; the organic layer was washed with 10% Na₂S₂O₃ (5 mL), dried (MgSO₄), and concentrated to a yellow oil, compound E10, (302.5 mg).

EXAMPLE 8

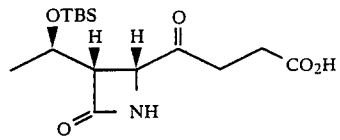

E11

The crude oil, compound E10 (4.6 g, 13.8 mol), was dissolved in methanol (82 mL); triethylamine (0.66 g, 6.6 mmol) and 10% Pd on carbon (0.25 g) was added. The mixture was hydrogenated at 40 psi H₂ for 1 hour at room temperature, filtered, and concentrated. The residue was dissolved in ether (50 mL), washed with 10% citric acid (20 mL), dried (MgSO₄) and concentrated to a yellow oil, compound E11 4.21 g, 12.8 mmol.

EXAMPLE 9

(1″R,3R,4R)-3-(1″-t-butyldimethylsilyloxyethyl)-4-acetoxyazetidin-2-one

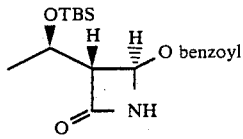
E12

The crude oil, compound E11, (329 mg, 1.0 mmol) was dissolved in methylene chloride (1.0 mL) and meta-chloroperbenzoic acid (mCPBA) (327 mg, 1.5 mmol) was added. The solution was stirred at 40° C. for 14 hours. A second portion of mCPBA (109 mg, 0.5 mmol) was added and the solution was heated at 40° C. for 16 hours. The solution was concentrated and the residue was dissolved in $CH_3CN$ (8 mL). Sodium benzoate (1.44 g, 10 mmol) in $H_2O$ (2.8 ml) was added and the pH adjusted to 9.2 by dropwise addition of dilute NaOH. The mixture was heated at 40° C. for 1 hour and then was stirred at 25° C. for 14 hours. Water (50 mL) was added and the mixture was extracted with $CH_2Cl_2$ (2×15 mL). The organic layer was dried ($Na_2SO_4$), concentrated, and chromatographed on silica gel (eluted with 3:1 hexane:ethyl acetate) giving 4 (R)-benzoyloxy-3(R)-[1(R)-dimethyl-1, 1-dimethylethylsilyloxyethyl]azetidinone, E12, (50.0 mg, 0.14 mmol).

EXAMPLE 10

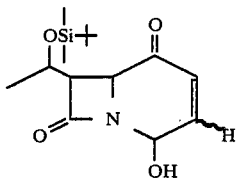

The following example demonstrates the use of bromine alone as the oxidation catalyst. Bromine (0.4 mL of 0.8M solution in $CH_3CN$, 0.32 mmol) was added to compound E9 (80.2 mg, 0.27 mmol) in $CH_3CN$ (1 mL) and 1M $K_2CO_3$ (1 mL) at 0° C. After stirring 10 min., $CH_2Cl_2$ (10 mL) was added and the mixture was washed with 10% $Na_2S_2O_3$ solution (10 mL), dried ($Na_2SO_4$) and concentrated to an oil. Chromatography on silica gel (1:2 hexane:ethyl acetate) provided the purified diastereomers, less polar 33.2 mg, more polar 28.7 mg (total 73%).

What is claimed is:

1. A method for the production of 4-acyloxyazetidin-2-ones comprising the steps of:
   (a) contacting, at temperatures from about 0°–20° C., an oxidizing combination comprising about 2 to about 150 mole % bromine based on 4-furanyl compound, and sufficient sodium chlorite to produce 4-hydroxylactone azetidin-2-one with 4-furanyl compound of the formula:

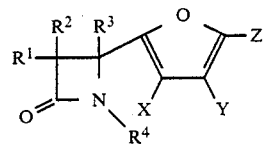

wherein $R^1$ and $R^2$ are independently selected from the group consisting of hydrogen, $C_{1-10}$ alkyl, $C_{1-10}$ fluoroalkyl, alpha-carbon substituted $C_{1-10}$ alkyl, alpha-carbon substituted $C_{1-10}$ fluoroalkyl, where the alpha-carbon substituent is selected from the group consisting of hydroxyl and protected hydroxyl; $R^3$ is selected from the group consisting of hydrogen and $C_{1-10}$ alkyl; $R^4$ is selected from the group consisting of hydrogen and a protecting group for nitrogen; and X, Y and Z are independently selected from the group consisting of hydrogen, halogen, $C_{1-10}$ alkyl, $C_6$ or $_{10}$ aryl, $C_{1-10}$ alkoxy, $C_6$ or $_{10}$ aryloxy.

2. The method of claim 1 wherein said contacting step (a) is followed by the steps:
   (b) hydrogenating said 4-hydroxylactone azetidin-2-one; and
   (c) contacting the reaction product of step (b) with a peracid to react to 4-acyloxyazetidin-2-one.

3. The method of claim 2 wherein said contacting step (c) is followed by the step of:
   (d) contacting said 4-acyloxyazetidin-2-one with an excess of alkali metal salt of a $C_{1-8}$ organic acid.

4. The method of claim 1 wherein $R^4$ is hydrogen.

5. The method of claim 1 wherein said oxidizing combination comprises from about 5 to about 15 mole % bromine based on said 4-furanyl compound.

6. The method of claim 1 wherein said oxidizing combination comprises from 100–200 mole % sodium chlorite based on said 4-furanyl compound.

7. The method of claim 1 wherein either $R^1$ or $R^2$ is hydrogen.

8. The method of claim 1 wherein $R^2$ is beta-hydrogen and $R^1$ is other than hydrogen.

9. The method of claim 1 wherein $R^2$ is beta-hydrogen and $R^1$ is alpha oriented 1-hydroxyethyl.

10. The method of claim 1 wherein X, Y and Z are hydrogen.

11. An oxidizing combination comprising relative to 100 moles organic material to be oxidized.
   (a) about 2 to about 150 moles bromine; and
   (b) about 100 to about 200 moles sodium chlorite.

12. The combination of claim 11 comprising 5 to 15 moles bromine.

* * * * *